United States Patent [19]
Wolf

[11] Patent Number: 5,507,963
[45] Date of Patent: Apr. 16, 1996

[54] CONDENSATION PRODUCTS OF MELAMINE, (BENZO) TRIAZOLES AND ALDEHYDES

[75] Inventor: Jean-Pierre Wolf, Courtaman, Switzerland

[73] Assignee: Ciba-Geigy Corporation, Tarrytown, N.Y.

[21] Appl. No.: 432,413

[22] Filed: May 3, 1995

[51] Int. Cl.$^6$ .................. C10M 133/42; C07D 403/00
[52] U.S. Cl. .................. 252/50; 252/47; 252/51; 252/51.5 R; 252/77; 544/198
[58] Field of Search .................. 544/198; 252/50

[56] References Cited

U.S. PATENT DOCUMENTS

| | | | |
|---|---|---|---|
| 3,250,708 | 5/1966 | Dazzi et al. | 252/568 |
| 3,753,986 | 8/1973 | Singhal et al. | 544/198 |
| 4,376,836 | 3/1983 | Wiezer et al. | 544/198 |
| 4,683,071 | 7/1987 | Regenass et al. | 252/49.3 |
| 4,701,273 | 10/1987 | Brady et al. | 252/32.5 |
| 4,972,010 | 11/1990 | Wheeler et al. | 544/198 |
| 4,997,585 | 3/1991 | Frankenfeld et al. | 252/50 |
| 5,198,130 | 3/1993 | Schumacher | 252/50 |
| 5,371,218 | 12/1994 | Cipolli et al. | 544/198 |

OTHER PUBLICATIONS

Katritzky et al. J. Chem. Soc. Perkin Trans. I, 1989 pp. 639–642.

*Primary Examiner*—Ellen M. McAvoy
*Attorney, Agent, or Firm*—Michele A. Kovaleski

[57] ABSTRACT

There are described compounds of formula I

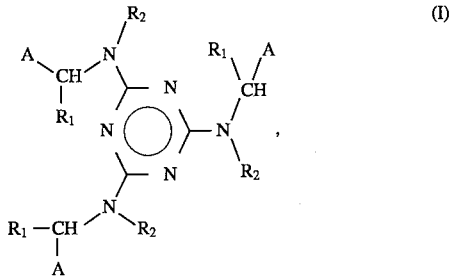

wherein
A is

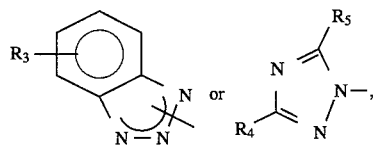

and $R_1$ to $R_5$ are as defined in claim 1. Said compounds are suitable for use as metal deactivators.

17 Claims, No Drawings

CONDENSATION PRODUCTS OF MELAMINE, (BENZO) TRIAZOLES AND ALDEHYDES

The invention relates to novel compounds which contain triazine groups and benzotriazole groups and which are suitable in particular for use as metal deactivators and corrosion inhibitors, to compositions comprising said compounds and to the use thereof.

It is common knowledge that copper ions catalyst the autoxidation as well as the formation of peroxide radicals in organic materials. The same applies to the oxidative degradation of lubricants (q.v. Ullmanns Encyclopedia of Industrial Chemistry, Vol. A3, p. 104). The addition of benzotriazole or benzotriazole derivatives, usually together with antioxidants, is able to reduce very substantially the acceleration of the degradation of the lubricant by copper.

The compounds currently used in practice are typically those of the

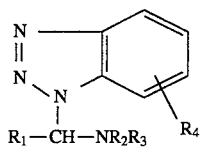

type, wherein e.g. $R_1$ is hydrogen, $R_2$ and $R_3$ are 2-ethylhexyl or hydroxyethyl, and $R_4$ is hydrogen or methyl (q.v. for example U.S. Pat. Nos. 4,683,071 and 4,701,273).

Katritzky et al. describe as intermediates N-substituted benzotriazoles of the above formula, wherein $R_1$ is propyl or butyl, $R_2$ and $R_4$ are hydrogen and $R_3$ is, inter alia, pyridyl (A. R. Katritzky, J.-J. Vanden Eynde, J. Chem. Soc. Perkin Trans. 1989, 639).

U.S. Pat. No. 4,997,585 discloses, for example, the compound of the above formula as oil additive, wherein $R_1$ is n-heptyl, $R_2$ is phenyl, and $R_3$ and $R_4$ are hydrogen.

There is still a need for active compounds having metal deactivating or corrosion-inhibiting properties.

It has now been found that the compounds containing triazine radicals and (benzo)triazole radicals and described hereinafter in more detail, have excellent metal deactivating and corrosion-inhibiting properties. The activity is further enhanced by further adding to the lubricant a suitable antioxidant or mixture of antioxidants.

Accordingly, the invention relates to compounds of formula I

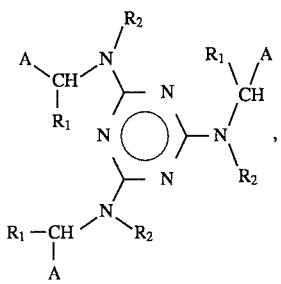 (I)

wherein

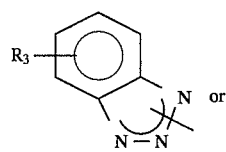 (II)

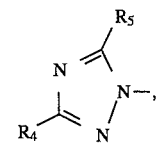 or

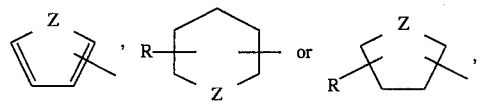 (III)

A is $R_1$ is hydrogen, $C_1$–$C_{20}$alkyl, $C_2$–$C_{20}$alkenyl, $C_5$–$C_{12}$cycloalkyl, or $C_5$–$C_{12}$cycloalkyl which is substituted by $C_1$–$C_{10}$alkyl; phenyl, naphthyl; phenyl or naphthyl, each of which is substituted by $C_1$–$C_{10}$alkyl, $C_1$–$C_{10}$alkoxy, halogen, hydroxy, nitro or phenoxy; a group, of formula wherein R is hydrogen or $C_1$–$C_{10}$alkyl, and Z is oxygen, sulfur, —NH—, —NR$_6$— or a methylene group, or $R_1$ is COOR$_7$, $R_2$ is hydrogen, $C_1$–$C_{20}$alkyl or $C_5$–$C_{12}$cycloalkyl, $R_3$ is hydrogen, $C_1$–$C_5$alkyl, $C_1$–$C_5$alkoxy, hydroxy, halogen, nitro, carboxy or $C_2$–$C_{11}$alkoxycarbonyl, $R_4$ and $R_5$ are each independently of the other —SH, —NH$_2$, —NHR$_6$, —NO$_2$, —COOH, —SR$_6$, —N(R$_6$)$_2$, —COO—R$_6$ or maleimido, $R_6$ is $C_1$–$C_{10}$alkyl, $R_7$ is hydrogen, M$^{n+}$/n or [NR$_8$R$_9$R$_{10}$R$_{11}$]$^+$, M is alkali or alkaline earth metal alkali, n is 1 or 2, and $R_8$ to $R_{11}$ are each independently of one another hydrogen, $C_1$–$C_8$alkyl or $C_1$–$C_8$hydroxyalkyl.

Suitable compounds are those of formula I, wherein $R_1$ is hydrogen, $C_1$–$C_{18}$alkyl, $C_2$–$C_{18}$alkenyl, phenyl, cyclohexyl, $C_1$–$C_4$ alkyl-substituted cyclohexyl, or COOR$_7$, $R_2$ is hydrogen, $C_1$–$C_{12}$alkyl or cyclohexyl, $R_3$ is hydrogen, Cl, methyl, methoxy, hydroxy or nitro, and $R_4$ and $R_5$ are each independently of the other hydrogen, SH, NH$_2$ or NO$_2$.

Preferred compounds are those of formula I, wherein $R_1$ is $C_1$–$C_{12}$alkyl, cyclohexyl, phenyl, COOH, or COOR$_7$, and also those compounds wherein $R_2$, $R_4$ and $R_5$ are hydrogen, as well as those compounds wherein $R_3$ is hydrogen, $C_1$–$C_5$alkyl, $C_1$–$C_5$alkoxy or hydroxy.

Particularly preferred compounds are those of formula I, wherein $R_1$ is $C_1$–$C_{12}$alkyl, $C_2$–$C_{12}$alkenyl, COOR$_7$ or phenyl, and those compounds wherein $R_3$ is hydrogen, butyl or methyl, and also those compounds wherein $R_2$ is hydrogen or $C_1$–$C_4$alkyl, as well as those compounds wherein $R_4$ and $R_5$ are H.

Particularly preferred compounds are also those of formula I, wherein $R_2$, $R_3$, $R_4$ and $R_5$ are hydrogen or $C_1$–$C_4$-alkyl, and $R_1$ is $C_1$–$C_{12}$alkyl, phenyl, COOH, or COOR$_7$.

A suitable embodiment of the invention comprises compounds of formula Ia,

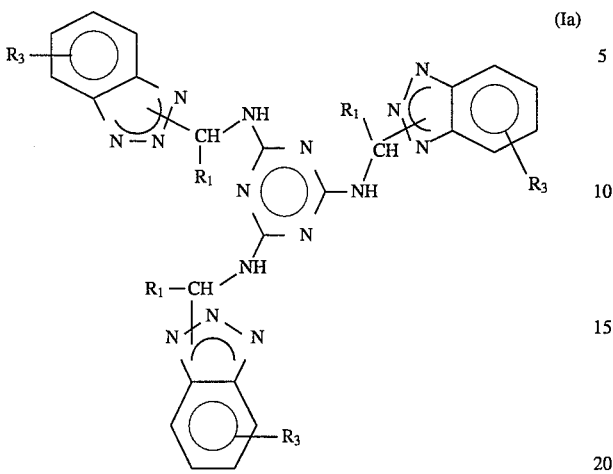

wherein $R_1$ is hydrogen, $C_1$-$C_{20}$alkyl, $C_2$-$C_{20}$alkenyl, $C_5$-$C_{12}$cycloalkyl, or $C_5$-$C_{12}$cycloalkyl which is substituted by $C_1$-$C_{10}$alkyl; phenyl, naphthyl; phenyl or naphthyl, each of which is substituted by $C_1$-$C_{10}$alkyl, $C_1$-$C_{10}$alkoxy, halogen, hydroxy, nitro or phenoxy; a group of formula

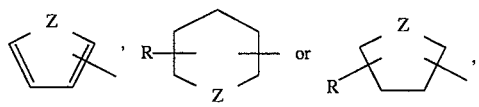

wherein R is hydrogen or $C_1$-$C_{10}$alkyl, Z is oxygen or sulfur, and $R_3$ is hydrogen, $C_1$-$C_5$alkyl, $C_1$-$C_5$alkoxy, hydroxy, halogen, nitro, carboxy or $C_2$-$C_{11}$alkoxycarbonyl, preferably hydrogen, $C_1$-$C_5$alkyl, $C_1$-$C_5$alkoxy or hydroxy. $R_1$ is preferably $C_1$-$C_{12}$alkyl, $C_2$-$C_{12}$alkenyl or phenyl.

Particularly suitable compounds are those of formula Ia, wherein $R_3$ is hydrogen, $C_1$-$C_5$alkyl, $C_1$-$C_5$alkoxy or hydroxy, as well as those compounds of formula Ia, wherein $R_1$ is $C_1$-$C_{12}$alkyl, $C_2$-$C_{12}$alkenyl or phenyl.

$C_1$-$C_{20}$Alkyl radicals may be straight-chain or branched and, depending on the number of carbon atoms indicated, are typically methyl, ethyl, propyl, isopropyl, n-butyl, isobutyl, t-butyl, pentyl, isopentyl, hexyl, heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1-methylundecyl or eicosyl.

If radicals or the substituents thereof are groups containing a lower number of carbon atoms, then corresponding examples are likewise to be found in the above list.

$R_3$ defined as alkyl preferably contains 1 to 4 carbon atoms and is in particular methyl.

$[NR_8R_9R_{10}R_{11}]^\oplus$ is preferably ammonium or $^\oplus H_3N$-$C(CH_3)_2$-$CH_2$-OH.

$C_2$-$C_{20}$Alkenyl may be branched or straight-chain. Typical examples are: vinyl, allyl, methallyl, hexenyl, decenyl, undecenyl, dimethyloctadienyl (geranyl, noryl), undecenyl, heptadecenyl and oleyl.

$C_5$-$C_{20}$Cycloalkyl is, for example, cyclopentyl, cyclohexyl, cyclooctyl or cyclododecyl. Cycloalkyl radicals of 5 to 8, more particularly of 5 or 6, carbon atoms are preferred, and cyclohexyl is particularly preferred. Typical examples of alkyl-substituted cycloalkyl groups are methylcyclohexyl and 4-butylcyclohexyl.

Halogen is chloro, fluoro, iodo or bromo, preferably chloro.

The structural unit

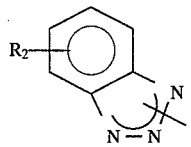

of formulae I and Ia will be taken to indicate that the benzotriazole may in each case be substituted in 1- or 2-position.

The preparation of the compounds is carried out by customary methods of organic chemistry (q.v.A.R. Katritzky, J.-J. Vanden Eynde, J. Chem. Soc. Perkin Trans. 1989, 639), e.g. according to the following equation:

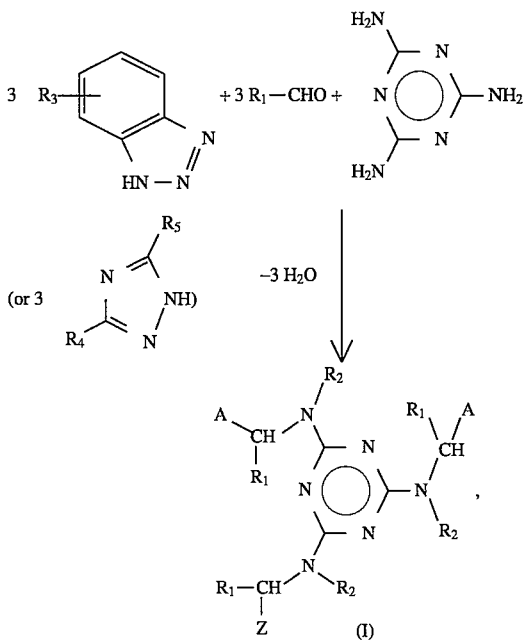

wherein

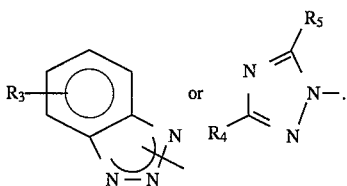

It may be the case that the reaction is not quite complete, resulting in only one or two (benzo)triazole groups being contained in the molecule. These by-products may be isolated by known separation methods such as chromatography. The by-products do not interfere with the known utilities. The invention also relates to said by-products as well as to mixtures of such by-products with the novel compounds.

Condensation can be carried out in non-polar organic solvents by acid catalysis conveniently with p-toluenesulfonic acid. The compounds may also be prepared in alcohols or in a mixture of alcohol and water, typically in ethanol, methanol or mixtures thereof with water. In these circumstances the use of an acid catalyst can be dispensed with.

As mentioned above, the products may be substituted in the 1- or 2-position of the benzotriazole system (1-benzotriazolyl compounds or 2-benzotriazolyl compounds). A separation of possible isomers is not necessary, but can be carried out by customary methods, e.g. by chromatography.

The starting materials employed are commercially available or may be prepared in accordance with known processes. It is to be mentioned that where methylbenzotriazole is used, the use of a mixture of 4- and 5-methylbenzotriazole is preferred.

The novel compounds are admirably suited for use as metal deactivators and antioxidants for organic materials which come into contact with metals or which contain metal ions as impurities. Furthermore, there is a marked antiwear activity with respect to lubricants. Accordingly, the invention also relates to compositions comprising a1) a lubricant, a machining fluid or a hydraulic fluid, or a2) a coating composition, in particular a paint system, and b) at least one compound of formula I, the preferred compounds cited above resulting in preferred compositions.

The compounds of formula I participate in the prevention of oxidative and degradative processes by binding, and thereby deactivating in particular copper ions. Accordingly, the invention also relates to the use of compounds of formula I as additives in lubricants, hydraulic fluids, machining fluids and coating compositions, in particular as metal deactivators and corrosion inhibitors.

Suitable lubricants, machining fluids and hydraulic fluids are typically based on mineral oils or synthetic oils or mixtures thereof. The lubricants are known to the skilled person and described in the relevant literature, for example in Dieter Klamann, "Schmierstoffe and verwandte Produkte" (Verlag Chemie, Weinheim, 1982), in Schewe-Kobek, "Das Schmiermittel-Taschenbuch" (Dr. Alfred H üthig-Verlag, Heidelberg, 1974) and in "Ullmanns Enzyklop ädie der technischen Chemie", Vol. 13, pages 85–94 (Verlag Chemie, Weinheim, 1977).

The lubricants are preferably oils and fats based, for example, on a mineral oil. The oils are preferred.

A further group of lubricants which may be used are vegetable or animal oils, fats, tallows and waxes or the mixtures thereof with one another or with the cited mineral or synthetic oils. Vegetable and animal oils, fats, tallows and waxes are, for example, palm nut oil, palm oil, olive oil, beet oil, rape oil, linseed oil, groundnut oil, soybean oil, cotton seed oil, sunflower seed oil, pumpkin seed oil, coconut oil, corn oil, castor oil, walnut oil and mixtures thereof, fish oils, tallows of slaughter animals such as beef tallow, neat's foot oil and bone oil as well as their modified, epoxidised and sulfoxidised forms, e.g. epoxidised soybean oil.

The mineral oils are preferably based on hydrocarbon compounds.

Synthetic lubricants typically comprise lubricant compositions based on aliphatic or aromatic carboxylates, polymeric esters, polyalkylene oxides, phosphates, poly-α-olefins or silicones, on a diester of a divalent acid with a monohydric alcohol, for example dioctyl sebacate or dinonyl adipate, on a triester of trimethylolpropane with a monovalent acid or with a mixture of such acids, for example trimethylolpropane tripelargonate, trimethylolpropane tricaprylate or mixtures thereof, on a tetraester of pentaerythritol with a monovalent acid or with a mixture of such acids, for example pentaerythritol tetracaprylate, or on a complex ester of monovalent and divalent acids with polyhydric alcohols, for example a complex ester of trimethylolpropane with caprylic and sebacic acid or of a mixture thereof. Especially suitable are, in addition to mineral oils, for example poly-α-olefins, ester-based lubricants, phosphates, glycols, polyglycols and polyalkylene glycols, and mixtures thereof with water.

Machining fluids and hydraulic fluids may be prepared on the basis of the substances described above for the lubricants. Those fluids are also often emulsions of such substances in water or other liquids.

The lubricant compositions of this invention are used, for example, in combustion engines, e.g. in motor vehicles fitted with motors of the otto-cycle, diesel, two-stroke or orbital type.

The compounds of formula I are readily soluble in lubricants, machining fluids and hydraulic fluids and are therefore particularly suitable for use as additives to lubricants, machining fluids and hydraulic fluids.

Accordingly, the present invention also relates to a process for enhancing the performance properties of lubricants, machining fluids and hydraulic fluids, which comprises adding thereto compounds of formula I.

The compounds of formula I may be blended with the lubricants in per se known manner. The compounds are, for example, readily soluble in oils. It is also possible to prepare a master-batch which may be diluted with the corresponding lubricant to concentrations for application. In such cases it is also possible to use concentrations above 10% by weight.

The novel compounds described above may be present in the lubricant, the machining fluid or the hydraulic fluid in amounts of, for example, 0.01 to 10% by weight, conveniently of 0.05 to 5% by weight, preferably of 0.05 to 3% by weight and, most preferably, of 0.05 to 1.5% by weight, based on the composition.

In addition to the novel compounds, the lubricants, machining fluids and hydraulic fluids may contain further customary additives, such as further antioxidants, metal deactivators, rust inhibitors, viscosity index improvers, pour-point depressants, dispersants/surfactants and extreme pressure/antiwear additives.

Illustrative examples are:

Examples of phenolic antioxidants:

1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl- 4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis( 6-tert-butyl-2-methylphenol), 4,4'-thiobis-(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis [4-methyl-6-(α -methylcyclohexyl)], 2,2'-methylenebis(4-methyl-6-cyclohexylphenol), 2,2'-methylenebis( 6-nonyl-4-methylphenol), 2,2'-methylenebis(4,6-di-tert-butylphenol), 2,2'-ethylidenebis( 4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl] terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3', 5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine compounds, for example 2,4-bis(octylmercapto)-6-(3,5-di-tert-butyl-4-hydroxyanilino-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-( 3,5-di-tert-butyl-4-hydroxybenzyl)isocyanurate, 1,3,5-tris(4-tert-butyl-3-hydroxy-2,6-dimethylbenzyl)isococyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols., for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21]octane.

1.13. Esters of β(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

1.17. Tocopherols, for example α-tocopherol, β-tocopherol, γ-tocopherol, δ-tocopherol and mixtures thereof (vitamin E).

Examples of aminic antioxidants:

N,N'-diisopropyl-p-phenylenediamine, N,N'-di-sec-butyl-p-phenylenediamine, N,N'-bis-( 1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p- phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis-(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-di-methyl-4H-1,4-benzothiazine, phenothiazine, N-allylphenothiazine, N,N,N',N'-tetra-phenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one and 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:

a) benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutriazole.

b) 1,2,4-triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis(2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenylsuccinic acids and theft partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-carboxymethyl-1-dodecyl-3-methylglycerol and the amine salts thereof.

b) Nitrogen-containing compounds, for example:
  i. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
  ii. Heterocyclic compounds, for example:
  Substituted imidazolines and oxazolines, and 2-heptadecenyl-1-(2-hydroxyethyl)imidazoline.

c) Phosphorus-containing compounds, for example:
  Amine salts of phosphoric acid partial esters or phosphonic acid partial esters, and zinc dialkyldithiophosphates.

d) Sulfur-containing compounds, for example:
  Barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example:
  Glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of viscosity index improvers are:

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:

Polymethacrylate and alkylated naphthalene derivatives.

Examples of dispersants/surfactants are:

Polybutenylsuccinic amides or -imides, polybutenylphosphonic acid derivatives and basic magnesium, calcium and barium sulfonates and phenolates.

Examples of extreme pressure and antiwear additives are:

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thio]propionate, triphenyl thiophosphate (triphenylphosphorothioate), tris(alkylphenyl) phosphorothioate and mixtures thereof (for example tris(isononylphenyl) phosphorothioate), diphenyl mononorylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris[isooctyl2-acetate], derivatives of 2-mercaptobenzothiazole such as 1-[N,N-bis-(2-ethylhexyl)aminomethyl]-2-mercapto-1H-1,3-benzothiazole, and ethoxycarbonyl-5-octyldithiocarbamate.

The novel compounds are particularly effective together with phenolic and/or aminic antioxidants.

Coating compositions usually consist of binders, additives and, optionally, chromophoric components.

Suitable binders are in principle all those customary in the art, for example those described in Ullmann's Encyclopedia of Industrial Chemistry, 5. Ed., Vol. A18, pp. 368–426, VCH, Weinheim 1991. The binder is usually a film-forming binder based on a thermoplastic or thermocurable resin, preferably on a thermocurable resin. Typical examples are alkyd resins, acrylic resins, polyester resins, phenolic resins, melamine resins, epoxy resins, polyurethane resins and mixtures thereof.

The binder may be a cold-curable or hot-curable binder and the addition of a curing catalyst may be advantageous. Suitable catalysts which accelerate the full cure of the binder are described, inter alia, in Ullmann's Encyclopedia of Industrial Chemistry, Vol. A 18, p. 469, VCH Verlagsgesellschaft, Weinheim 1991. Preferred coating compositions are those containing as film-forming binder epoxy resins, polyurethane resins, polyester resins, acrylic resins and the copolymer resins thereof, polyvinyl resins, phenolic resins, alkyd resins or mixtures of such resins. The compounds of formula I may be contained in the coating compositions in an amount of 0.001 to 10%, preferably of 0.1 to 5%.

If the novel compositions are coating compositions or paint systems, then these may contain further customary components, typically selected from the group consisting of the dyes, pigments, fillers, flow control agents, adhesion promoters, curing catalysts, light stabilisers or antioxidants.

The preferred novel compounds described above result in preferred compositions.

The following Examples further illustrate the invention without, however, restricting it in any way. Parts and percentages are by weight, unless otherwise stated. The reactions are all carried out under nitrogen. If the products begin to crystallise already while the reaction solution is cooling, then they are isolated by filtration and further purification is dispensed with.

EXAMPLES 1 to 16

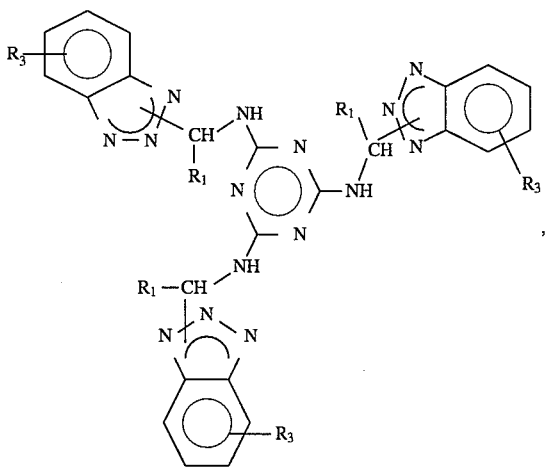

(Ia)

Example 1: In a four-necked flask equipped with mechanical stirrer, Dean-Stark water separator, thermometer and nitrogen inlet, 6.31 g (0.05 mol) of melamine, 19.97 g (0.15 mol) of tolyltriazole, 8.5 ml (0.15 mol) of acetaldehyde and 0.2 g of p-toluene-sulfonic acid are suspended under nitrogen in 100 ml of cyclohexane. The mixture is refluxed for 5 hours while distilling off the water of reaction as an azeotrope. The product is isolated by filtration and dried at 80° C. under vacuum, affording 20.2 g of an orange solid: product of formula Ia ($R_1$=$CH_3$; $R_3$=$CH_3$).

Example 2: In a four-necked flask equipped with mechanical stirrer, Dean-Stark water separator, thermometer and nitrogen inlet, 6.31 g (0.05 mol) of melamine, 19.97 g (0.15 mol) of tolyltriazole, 10.5 ml (0.15 mol) of butyraldehyde and 0.2 g of p-toluene-sulfonic acid are suspended under nitrogen in 100 ml of cyclohexane. The mixture is refluxed for 12 hours while distilling off the water of reaction as an azeotrope. To the reaction solution are added 300 ml of toluene. The batch is washed with 3×100 ml of a 5% solution of $Na_2CO_3$ and with 2×100 ml of water, dried over anhydrous $MgSO_4$ and the solvent is then distilled off, affording 21.4 g of an orange solid: product of formula Ia ($R_1$=$CH_3(CH_2)_2$, $R_3$=$CH_3$).

Example 2a: In a four-necked flask equipped with mechanical stirrer, reflux condenser, thermometer and nitrogen inlet, 6.31 g (0.05 mol) of melamine, 19.97 g (0.15 mol) of tolyltriazole and 13.5 ml (0.15 mol) of butyraldehyde are suspended under nitrogen in 300 ml of methanol. The suspension is refluxed for 14 hours and the solvent is distilled off, affording the product described in Example 2 in quantitative yield: an orange solid, product of formula Ia ($R_1$=$CH_3(CH_2)_2$, $R_3$=$CH_3$).

Examples 3, 4 and 5: In a four-necked flask equipped with mechanical stirrer, Dean-Stark water separator, thermometer and nitrogen inlet, 6.31 g (0.05 mol) of melamine, 19.97 g (0.15 mol) of tolyltriazole, 0.15 mol of the respective aldehyde (q.v. Table I) and 0.2 g of p-toluenesulfonic acid are suspended under nitrogen in 100 ml of toluene. The mixture is refluxed for 5 or 12 hours (see Table I) while distilling off the water of reaction as an azeotrope. The reaction solution is washed with 3×100 ml of a 5% solution of $Na_2CO_3$ and with 2×100 ml of water and then dried over anhydrous $MgSO_4$. The solvent is then distilled off, affording in each case yellowish solids.

Example 3: Product of formula Ia ($R_1$=$CH_3(CH_2)_5$, $R_3$=$CH_3$), m.p. 108°–26° C.

Example 4: Product of formula Ia ($R_1$=$CH_3(CH_2)_{10}$, $R_3$=$CH_3$) m.p. 58°–75° C.

Example 5: Product of formula Ia ($R_1$=$C_6H_5$, $R_3$=$CH_3$) m.p. 122°–138° C.

Example 6: In a four-necked flask equipped with mechanical stirrer, reflux condenser, thermometer and nitrogen inlet, 12.62 g (0.1 mol) of melamine, 27.62 g (0.3 mol) of glyoxylic acid monohydrate and 30.95 g (0.3 mol) of tolyltriazole are suspended under nitrogen in 150 ml of ethanol and 150 ml of water. The mixture is refluxed for 5 hours and then cooled to room temperature. The product is isolated by filtration, washed with 200 ml of water and dried at 70° C. in a vacuum drying oven, affording 10.3 g (15% of theory) of a whitish solid.

Product of formula Ia ($R_3$=$CH_3$, $R_1$=$CO_2H$)

Example 7 (Amine salt): 3.46 g (0.005 mol) of the compound of Example 6 and 1.5 ml (0.015 mol) of 2-amino-2-methyl-1-propanol are dissolved in 17.3 ml of water and stirred for 1 hour at room temperature. The water is distilled off on a rotary evaporator, affording 4.56 g (95% of theory) of a yellowish vitreous solid.

Product of formula Ia ($R_3$=$CH_3$, $R_1$=$CO_2^{\ominus \oplus}H_3N$—$C(CH_3)_2$—$CH_2$—OH Solubility in water: 5% at room temperature Example 8 (Sodium salt): In a four-necked flask equipped with mechanical stirrer, reflux condenser and thermometer, 20.81 g (0.03 mol) of the compound of Example 6 and 3.6 g (0.09 mol) of NaOH are suspended in 22.5 ml of water. The suspension is stirred for 3 hours at 80° C. and then cooled to room temperature, affording an orange-red clear and slightly viscous solution of the salt.

Product of formula Ia ($R_3=CH_3$, $R_1=CO_2Na$)

TABLE I

Tolyltriazole derivatives ($R_3 = CH_3$)

| Compound of Example | Aldehyde | Reflux time | Yield | Elemental analysis of the product obtained calculated (found) | | |
|---|---|---|---|---|---|---|
| | | | | % C | % H | % N |
| 1 | $CH_3CHO$ | 5 h | 67% | 59.7 (58.3) | 5.5 5.5 | 34.8 34.6) |
| 2 | $CH_3(CH_2)_2CHO$ | 12 h | 62% | 62.9 (64.1) | 6.6 7.1 | 30.5 25.5) |
| 3 | $CH_3(CH_2)_5CHO$ | 5 h | 65% | 66.4 (65.9) | 7.8 8.1 | 25.8 26.2 |
| 4 | $CH_3(CH_2)_{10}CHO$ | 12 h | 45% | 70.3 (70.6) | 9.2 9.3 | 20.5 19.8) |
| 5 | $C_6H_5CHO$ | 5 h | 39% | 68.4 (67.9) | 5.0 5.3 | 26.6 26.2) |

| | | Acid number [mg KOH/g] | m.p. [°C.] |
|---|---|---|---|
| 6 | $HCO-CO_2H$ | | 228 (dec.) |
| 7 | (Amine salt of 6) | 203 | 80–125 |

Examples 9 and 14: In a four-necked flask equipped with mechanical stirrer, Dean-Stark water separator, thermometer and nitrogen inlet, 6.31 g (0.05 mol) of melamine, 17.87 g (0.15 mol) of benzotriazole, 0.15 mol of paracetaldehyde or paraformaldehyde and 0.2 g of p-toluenesulfonic acid are suspended under nitrogen in 100 ml of toluene. The mixture is refluxed for 5 hours while distilling off the water of reaction as an azeotrope. The product is isolated by filtration and dried at 80° under reduced pressure, affording in each case yellowish-orange solids.

Example 9: Product of formula Ia ($R_1=CH_3$, $R_3=H$), m.p. 95° C.

Example 14: Product of formula Ia ($R_1=H$, $R_3=H$), m.p. 193°–212° C.

Example 10: In a four-necked flask equipped with mechanical stirrer, Dean-Stark water separator, thermometer and nitrogen inlet, 6.31 g (0.05 mol) of melamine, 17.87 g (0.15 mol) of benzotriazole, 13.5 ml (0.15 mol) of butyraldehyde and 0.2 g of p-toluene-sulfonic acid are suspended under nitrogen in 100 ml of toluene. The mixture is refluxed for 5 hours while distilling off the water of reaction as an azeotrope. The solvent is decanted off and the tacky residue is dissolved in methylene chloride. The solvent is then distilled off, affording 8.87 g of a yellowish-orange solid:

Product of formula Ia ($R_1=CH_3(CH_2)_2$, $R_3=H$), m.p 74°–92° C.

Examples 11, 12 and 13: In a four-necked flask equipped with mechanical stirrer, Dean-Stark water separator, thermometer and nitrogen inlet, 6.31 g (0.05 mol) of melamine, 17.87 g (0.15 mol) of benzotriazole, 0.15 mol of the respective aldehyde (q.v. Table II) and 0.2 g of p-toluenesulfonic acid are suspended under nitrogen in 100 ml of toluene. The mixture is refluxed for 4 or 5 hours (see Table II) while distilling off the water of reaction as an azeotrope. The reaction solution is washed with 3×100 ml of a 5% solution of $Na_2CO_3$ and with 2×100 ml of water, dried over anhydrous $MgSO_4$ and the solvent is then distilled off, affording in each case yellow solids:

Example 11: Product of formula Ia ($R_1=CH_3(CH_2)_5$, $R_3=H$), m.p. 79°–89° C.

Example 12: Product of formula Ia ($R_1=CH_3(CH_2)_{10}$, $R_3=H$), vitreous resin Example 13: Product of formula Ia ($R_1=C_6H_5$, $R_3=H$), m.p. 130°–142° C.

Example 15: In a four-necked flask equipped with mechanical stirrer, reflux condenser, thermometer and nitrogen inlet, 12.62 g (0.1 mol) of melamine, 27.62 g (0.3 mol) of glyoxylic acid and 35.74 g (0.3 mol) of benzotriazole are suspended under nitrogen in 150 ml of ethanol and 150 ml of water. The mixture is refluxed for 5 hours and cooled to room temperature. The product is isolated by filtration, washed with 200 ml of water and then dried in a vacuum drying oven at 70° C., affording 16.9 g (26% of theory) of a whitish solid.

Product of formula Ia ($R_3=H$, $R_1=CO_2H$)

Example 16: 6.51 g (0.01 mol) of the compound of Example 15 and 2.68 g (0.03 mol) of 2-amino-2-methyl-1-propanol are dissolved in 100 ml of water and stirred for 1 hour at room temperature. The water is distilled off on a rotary evaporator, affording 7.4 g (81% of theory) of a yellowish vitreous solid.

Product of formula Ia ($R_3=H$, $R_1=CO_2^{\ominus\oplus}H_3N-C(CH_3)_2-CH_2-OH$) Solubility in water: 5% at room temperature

TABLE II

Benzotriazole derivatives ($R_3 = H$)

| Example | Aldehyde | Reflux time | Yield | Elemental analysis of the product obtained calculated (found) | | |
|---|---|---|---|---|---|---|
| | | | | % C | % H | % N |
| 9 | $(CH_3CHO)_n$ | 5 h | 44% | 57.7 (59.7) | 4.8 4.2 | 37.4 35.5) |
| 10 | $CH_3(CH_2)_2CHO$ | 5 h | 62% | 61.4 (61.4) | 6.1 5.9 | 32.5 31.0) |
| 11 | $CH_3(CH_2)_5CHO$ | 5 h | 65% | 65.3 (64.5) | 7.4 7.3 | 27.2 25.5) |
| 12 | $CH_3(CH_2)_{10}CHO$ | 4 h | 45% | 69.7 (70.7) | 8.9 8.9 | 21.4 18.7) |
| 13 | $C_6H_5CHO$ | 4 h | 39% | 67.5 (67.1) | 4.5 4.8 | 28.1 26.6) |
| 14 | $(HCHO)_n$ | 5 h | 85% | 55.5 (54.2) | 4.1 4.3 | 40.4 40.6) |

| | | Acid number [mg KOH/g] | m.p. [°C.] |
|---|---|---|---|
| 15 | $HCO-CO_2H$ | | 234 (dec.) |
| 16 | (Amine salt of 15) | 183 | 80–125 |

EXAMPLES 17 TO 25

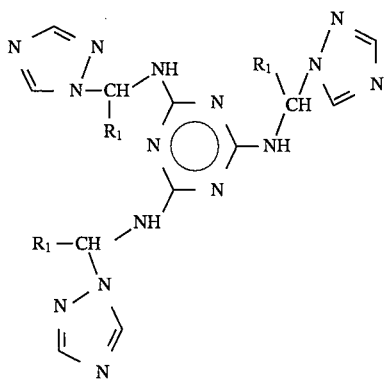

Example 17: In a four-necked flask equipped with mechanical stirrer, reflux condenser, thermometer and nitrogen inlet, 6.31 g (0.05 mol) of melamine, 10.35 g (0.15 mol) of 1,2,4-triazole and 12.5 g (0.15 mol) of formaldehyde (36% aqueous solution) are suspended under nitrogen in 300 ml of methanol. The mixture is refluxed for 12 hours and filtered to remove any unreacted educt. The filtrate is then concentrated by evaporation and the white residue is dried under vacuum (0.1 torr, 80° C.), to give the product in 70.3% yield: product of formula Ib ($R_1$=H).

Example 18: In a four-necked flask equipped with mechanical stirrer, Dean-Stark water separator, thermometer and nitrogen inlet, 6.31 g (0.05 mol) of melamine, 10.35 g (0.15 mol) of 1,2,4-triazole, 4.5 g (0.15 mol) of paraformaldehyde and 0.1 g of p-toluene-sulfonic acid are suspended under nitrogen in 100 ml of toluene. The mixture is refluxed for 2 hours while distilling off the water of reaction as an azeotrope. The product is isolated by filtration, recrystallised from water, and the product is then dried under vacuum (0.1 torr, 150° C.), affording a white solid in a yield of 43% of theory: product of formula Ib ($R_1$=H).

Example 19: In a four-necked flask equipped with mechanical stirrer, reflux condenser, thermometer and nitrogen inlet, 12.62 g (0.1 mol) of melamine, 20.72 g (0.3 mol) of 1,2,4-triazole and 27.5 ml (0.5 mol) of acetaldehyde are suspended under nitrogen in 300 ml of methanol. The mixture is refluxed for 20 hours and then concentrated by evaporation on a rotary evaporator. The pink residue is dried for 3 days at 60° C. in a vacuum drying oven.

Yield: 94% of theory Product of formula Ib ($R_1$=$CH_3$)

Examples 20 to 23: In a four-necked flask equipped with mechanical stirrer, Dean-Stark water separator, thermometer and nitrogen inlet, 6.31 g (0.05 mol) of melamine, 10.35 g (0.15 mol) of 1,2,4-triazole, 0.15 mol of the respective aldehyde (q.v. Table III) and 0.1 g of p-toluenesulfonic acid are suspended under nitrogen in 100 ml of toluene. The mixture is refluxed for the time stated in Table III while distilling off the water of reaction as an azeotrope. The solvent is distilled off and each product is dried under vacuum (0.1 torr, 80° C.), affording a yellowish solid:

Example 20: Product of formula Ib ($R_1$=$CH_3(CH_2)_2$)

Example 21: Product of formula Ib ($R_1$=$CH_3(CH_2)_{10}$)

Example 22: Product of formula Ib ($R_1$=$C_6H_5$)

Example 23: Product of formula Ib ($R_1$=$CH_3(CH_2)_5$)

Example 24: In a four-necked flask equipped with mechanical stirrer, reflux condenser, thermometer and nitrogen inlet, 12.61 g (0.1 mol) of melamine, 27.62 g (0.3 mol) of glyoxylic acid monohydrate and 20.7 g (0.3 mol) of 1,2,4-triazole are suspended under nitrogen in 150 ml of ethanol and 150 ml of water. The mixture is refluxed for 22 hours and cooled to room temperature. To the suspension so obtained are added 500 ml of methylene chloride. The batch is stirred for 2 hours and the product is isolated by filtration. The product is washed with 50 ml of methylene chloride, isolated by filtration and dried at 60° C. in a vacuum drying oven, affording 19.3 g (33% of theory) of a yellowish solid.

Product of formula Ib ($R_1$=$CO_2H$)

Example 25: 5.02 g (0.01 mol) of the compound of Example 24 and 2.68 g (0.03 mol) of 2-amino-2-methyl-1-propanol are dissolved in 100 ml of water and stirred for 2 hours at room temperature. The water is then distilled off on a rotary evaporator, affording 6.1 g (81% of theory) of a yellow vitreous solid.

Product of formula Ib ($R_1$=$COO^{\ominus\oplus}H_3N$—$C(CH_3)_2$—$CH_2$—OH) Solubility in water: 5% at room temperature

TABLE III

| | 1,2,4-Triazole derivatives | | | | | |
|---|---|---|---|---|---|---|
| | | | | Elemental analysis of the product obtained calculated (found) | | |
| Example | Aldehyde | Reflux time | Yield | % C | % H | % N |
| 18 | $CH_2O$ | 2 h | 43% | 39.0 (38.9 | 4.1 4.2 | 56.9 52.4) |
| 19 | $CH_3CHO$ | 20 h | 94% | 43.8 (42.8 | 5.1 5.2 | 51.1 50.6) |
| 20 | $CH_3(CH_2)_2CHO$ | 12 h | 83% | 50.9 (50.2 | 6.7 7.4 | 42.4 35.4) |
| 21 | $CH_3(CH_2)_5CHO$ | 12 h | 82% | 57.9 (57.7 | 8.3 8.3 | 33.8 32.1) |
| 22 | $CH_3(CH_2)_{10}CHO$ | 9 h | 87% | 64.9 (65.6 | 9.8 10.1 | 25.2 23.3) |
| 23 | $C_6H_5CHO$ | 3 h | 80% | 60.3 (57.1 | 4.5 4.9 | 35.1 34.8) |

| | | Acid number [mg KOH/g] | m.p. [°C.] |
|---|---|---|---|
| 24 | HCO—$CO_2H$ | | 238 (dec.) |
| 25 | (Amine salt of 24) | 195 | 77–118 |

Use Examples

Example A1: Copper corrosion test (modified according to ASTM D-130)

0.05% by weight of the compound to be tested is dissolved in a turbine oil (viscosity: 29.7 $mm^2s^{-1}$ at 40° C. and 5.05 $mm^2s^{-1}$ at 100° C.; sulfur content: 0.22%). A further 50 ppm of elemental sulfur are added.

A copper sheet (60×10×1 mm), polished with silicon carbide, is completely immersed in the oil solution and left therein for 3 hours at 100° C. The copper sheet is then taken out of the oil and rinsed with petroleum ether. Evaluation is carried out according to the ASTM D 130 Copper Strip Corrosion Standard Chart (q.v. Table IV). The evaluation is carried out in accordance with a rating from 1 to 4:

1—no tarnishing

2—moderate tarnishing

3—strong tarnishing

4—corrosion

Within the ratings 1 to 4 a further gradation is made based on the degree of tarnishing on the samples. In the qualitative evaluation from A to E the rating of A is superior to B, B is superior to C etc. The Table shows the ratings of two sheets each (parallel evaluation).

TABLE IV

| Copper corrosion test | |
|---|---|
| Compound of Example No. | Evaluation |
| — | 3B/4A |
| 2 | 1A/1A |
| 3 | 1A/1A |
| 4 | 1A/1B |
| 12 | 1A/1A |
| 22 | 1A/1A |

Example A2: Rotary Bomb Oxidation Test (RBOT), ASTM D 2272

0.05% by weight of the compound to be tested is dissolved in a turbine oil (viscosity: 29.7 mm²s⁻¹ at 40° C. and 5.05 mm²s⁻¹ at 100° C.; sulfur content: 0.22%). Further are 0.1% of a phenolic antioxidant, 0.1% of an aminic antioxidant or 0.1% each of a phenolic and an aminic antioxidant (q.v. Table IV). 50 ml of the mixture so obtained and 5 ml of water are put into the test container containing a copper spiral as catalyst. The container is charged with oxygen until a pressure of 620 kPa is reached, closed and then rotated in a bath of 150° C. The time is measured within which the oxygen pressure falls by 172 kPa.

TABLE V

| Rotary Bomb Oxidation Test (RBOT) | | | |
|---|---|---|---|
| Compound of Example No. | Antioxidant A[1)] | Antioxidant B[2)] | Time [min.] |
| — | — | — | 34 |
| — | 0.1% | — | 143 |
| — | — | 0.1% | 80 |
| 4 | 0.1% | — | 447 |
| 4 | — | 0.1% | 336 |
| 4 | 0.1% | 0.1% | 597 |
| 12 | 0.1% | — | 479 |
| 12 | — | 0.1% | 392 |

[2)]Mixture of diphenylamine compounds, commercially available as Irganox ® L-57, q.v. US-5 073 278, col. 2, 1. 50
[1)]Mixture of tert-butylised phenols, available as Irganox ® L 140.

Example A3: Copper corrosion in water 0.05% by weight of the compound to be tested is dissolved in 75 ml of hard water (DIN 51360). A copper sheet (50×20×0.2 mm), polished with silicon carbide and weighed, is completely immersed in the solution and stored, tightly sealed, for 24 hours at 60° C. The sheet is then taken out of the solution, dipped for 15 sec. into a 5N solution of hydrochloric acid and then washed with deionised water and acetone. The copper sheet is dried and then weighed again. The evaluation of corrosion protection is based on the weight loss. Major loss of weight denotes strong corrosion, minor loss of weight denotes good protection against corrosion. Table VI lists the values of one assessment:

TABLE VI

| Copper corrosion test in water | |
|---|---|
| Compound of Example No. | Loss in weight [mg] |
| — | 6.6 |
| 19 | 1.4 |
| 7 | 0.6 |

TABLE VI-continued

| Copper corrosion test in water | |
|---|---|
| Compound of Example No. | Loss in weight [mg] |
| 16 | 0.4 |
| 25 | 1.0 |

Example A4: Test for suitability as extreme pressure and antiwear additive

The ASTM standard method D-2783-81 is used for testing,the suitability as antiwear additive, using the Shell four ball apparatus. The base oil is of the 150 SSU type, supplied by Mobil, to which oil is added the amount of the compound according to each Example listed in the Table. The average wear scar diameter WSD is measured at a load of 400N after a 1 hour operation at 25° C. and 1440 rpm (in mm).

The results obtained are listed in Table VII. Small diameter of the wear scar denotes suitability as antiwear additive.

TABLE VII

| Compound of Example | Amount added [%] | WSD [mm] |
|---|---|---|
| no addition | — | 0.93 |
| 4 | 0.25 | 0.64 |
|  | 1.0 | 0.60 |

What is claimed is
1. A compound of formula I

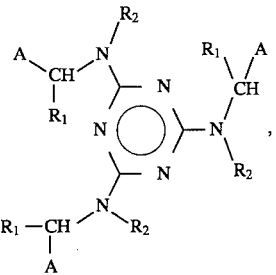

wherein
A is

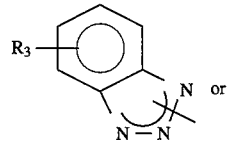

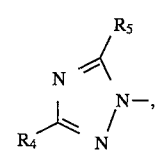

$R_1$ is hydrogen, $C_1$–$C_{20}$alkyl, $C_2$–$C_{20}$alkenyl, $C_5$–$C_{12}$cycloalkyl, or $C_5$–$C_{12}$cycloalkyl which is substituted by $C_1$–$C_{10}$alkyl; phenyl, naphthyl; phenyl or naphthyl, each of which is substituted by $C_1$–$C_{10}$alkyl, $C_1$–$C_{10}$alkoxy, halogen, hydroxy, nitro or phenoxy; a group of formula

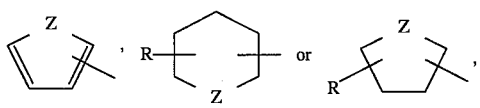

wherein R is hydrogen or $C_1$–$C_{10}$alkyl, and

Z is oxygen, sulfur, —NH—, —$NR_6$— or a methylene group, or $R_1$ is $COOR_7$, $R_2$ is hydrogen, $C_1$–$C_{20}$alkyl or $C_5$–$C_{12}$cycloalkyl, $R_3$ is hydrogen, $C_1$–$C_5$alkyl, $C_1$–$C_5$alkoxy, hydroxy, halogen, nitro, carboxy or $C_2$–$C_{11}$alkoxycarbonyl, $R_4$ and $R_5$ are each independently of the other —SH, —$NH_2$, —$NHR_6$, —$NO_2$, —COOH, —$SR_6$, —$N(R_6)_2$, —COO—$R_6$ or maleimido, $R_6$ is $C_1$–$C_{10}$alkyl, $R_7$ is hydrogen, $M^{n+}/n$ or $[NR_8R_9R_{10}R_{11}]^+$, M is alkali or alkaline earth metal, n is 1 or 2, and $R_8$ to $R_{11}$ are each independently of one another hydrogen, $C_1$–$C_8$alkyl or $C_1$–$C_8$hydroxyalkyl.

2. A compound according to claim 1, wherein $R_1$ is hydrogen, $C_1$–$C_{18}$alkyl, $C_2$–$C_{18}$alkenyl, phenyl, cyclohexyl, $C_1$–$C_4$alkyl-substituted cyclohexyl, or $COOR_7$, $R_2$ is hydrogen, $C_1$–$C_{12}$alkyl or cyclohexyl, $R_3$ is hydrogen, chloro, $C_1$–$C_5$alkyl, methoxy, hydroxy or nitro, $R_4$ and $R_5$ are each independently of the other hydrogen, SH, $NH_2$ or $NO_2$.

3. A compound according to claim 1, wherein $R_1$ is $C_1$–$C_{12}$alkyl, $C_2$–$C_{12}$alkenyl, cyclohexyl, $COOR_7$ or phenyl.

4. A compound according to claim 1, wherein $R_2$ is hydrogen or $C_1$–$C_4$alkyl.

5. A compound according to claim 1, wherein $R_1$ is $C_1$–$C_{12}$alkyl, phenyl, COOH, or $COOR_7$, and $R_2$, $R_3$, $R_4$ and $R_5$ are hydrogen or $C_1$–$C_4$alkyl.

6. A compound according to claim 1, wherein $R_3$ is hydrogen, $C_1$–$C_5$alkyl, $C_1$–$C_5$alkoxy or hydroxy.

7. A compound according to claim 1, wherein $R_3$ is hydrogen, methyl or butyl.

8. A compound of formula 1 according to claim 1, wherein $R_1$ is n-$C_{11}H_{20}$, $R_2$ is H, A is a radical II, and $R_3$ is $CH_3$; a compound according to claim 1, wherein $R_1$ is n-$C_{11}H_{23}$, $R_2$ is H, A is a radical II, and $R_3$ is H; a compound of formula I according to claim I, wherein $R_1$ is —COOH, $R_2$ is H, A is a radical II, and $R_3$ is $CH_3$; a compound of formula I according to claim I, wherein $R_1$ is COOH, A is a radical II, $R_2$ is H, and $R_3$ is H; and a compound of formula I according to claim I, wherein $R_1$ is $CH_3$, A is a radical III, $R_2$, $R_4$ and $R_5$ are H.

9. A compound according to claim 1, of formula Ia

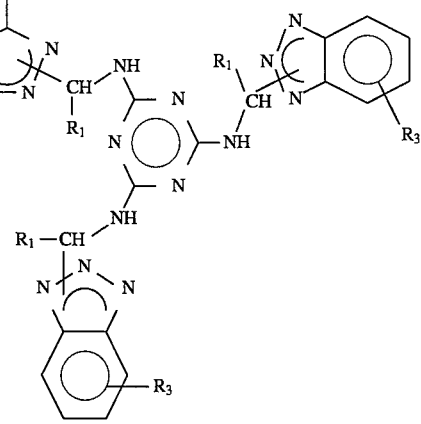

(Ia)

wherein $R_1$ is hydrogen, $C_1$–$C_{20}$alkyl, $C_2$–$C_{20}$alkenyl, $C_5$–$C_{12}$cycloalkyl, or $C_5$–$C_{12}$cycloalkyl which is substituted by $C_1$–$C_{10}$alkyl; phenyl, naphthyl; phenyl or naphthyl, each of which is substituted by $C_1$–$C_{10}$alkyl, $C_1$–$C_{10}$alkoxy, halogen, hydroxy, nitro or phenoxy; a group of formula

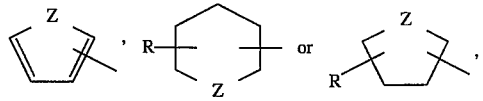

wherein R is hydrogen or $C_1$–$C_{10}$alkyl, Z is oxygen or sulfur, and $R_3$ is hydrogen, $C_1$–$C_5$alkyl, $C_1$–$C_5$alkoxy, hydroxy, halogen, nitro, carboxy or $C_2$–$C_{11}$alkoxycarbonyl.

10. A compound according to claim 9, wherein $R_3$ is hydrogen, $C_1$–$C_5$alkyl, $C_1$–$C_5$alkoxy or hydroxy.

11. A compound according to claim 9, wherein $R_1$ is $C_1$–$C_{12}$alkyl, $C_2$–$C_{12}$alkenyl or phenyl.

12. A composition comprising

A) a lubricant, a hydraulic fluid or a machining fluid, or a coating composition, and B) at least one compound of formula I, according to claim 1.

13. A composition according to claim 12, wherein component A) is a lubricant.

14. A composition according to claim 13, wherein the lubricant is a motor oil.

15. A composition according to claim 12, additionally comprising further stabilisers such as further antioxidants, further metal deactivators, rust inhibitors, viscosity index improvers, pour-point depressants, dispersants/surfactants and/or extreme pressure/antiwear additives.

16. A composition according to claim 15, comprising as further antioxidants phenolic and/or aminic antioxidants.

17. A process for enhancing the performance properties of lubricants, machining fluids or hydraulic fluids, which process comprises adding thereto a compound of formula I according to claim 1.

* * * * *

UNITED STATES PATENT AND TRADEMARK OFFICE
CERTIFICATE OF CORRECTION

PATENT NO. : 5,507,963
DATED      : April 16, 1996
INVENTOR(S) : Jean-Pierre Wolf It is certified that error appears in the above-indentified patent and that said Letters Patent is hereby corrected as shown below:

On the title page:
item [30] should read

--[30]   Foreign Application Priority Data

May 10, 1994  [CH]   Switzerland ............ 1459/94-1

Nov. 9, 1994  [CH]   Switzerland ............ 3374/94-3--.

Signed and Sealed this

Twenty-second Day of October, 1996

Attest:

BRUCE LEHMAN

*Attesting Officer*         *Commissioner of Patents and Trademarks*